United States Patent
Neuba et al.

(10) Patent No.: US 9,918,910 B2
(45) Date of Patent: *Mar. 20, 2018

(54) MULTI-TONAL ONE STEP DYEING WITH FOAM-TYPE PRE-TREATMENT SOLUTION

(71) Applicant: Henkel AG & Co. KGaA, Duesseldorf (DE)

(72) Inventors: Constanze Neuba, Grevenbroich (DE); Norbert Schettiger, Hilden (DE); Burkhard Mueller, Duesseldorf (DE)

(73) Assignee: Henkel AG & Co. KGaA (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/435,156

(22) Filed: Feb. 16, 2017

(65) Prior Publication Data

US 2017/0156996 A1      Jun. 8, 2017

Related U.S. Application Data

(63) Continuation of application No. PCT/EP2015/068561, filed on Aug. 12, 2015.

(30) Foreign Application Priority Data

Aug. 26, 2014    (DE) .................. 10 2014 216 941

(51) Int. Cl.
| | | |
|---|---|---|
| *A61Q 5/10* | (2006.01) | |
| *A61K 8/04* | (2006.01) | |
| *A61K 8/22* | (2006.01) | |
| *A61K 8/23* | (2006.01) | |
| *A61K 8/20* | (2006.01) | |
| *A61K 8/42* | (2006.01) | |
| *A61K 8/49* | (2006.01) | |
| *A61K 8/81* | (2006.01) | |
| *A61K 8/19* | (2006.01) | |
| *C11D 1/00* | (2006.01) | |

(52) U.S. Cl.
CPC ............. *A61K 8/046* (2013.01); *A61K 8/19* (2013.01); *A61K 8/20* (2013.01); *A61K 8/22* (2013.01); *A61K 8/23* (2013.01); *A61K 8/42* (2013.01); *A61K 8/4966* (2013.01); *A61K 8/8182* (2013.01); *A61Q 5/10* (2013.01); *C11D 1/00* (2013.01); *A61K 2800/4324* (2013.01)

(58) Field of Classification Search
CPC ............ A61K 8/046; A61K 8/22; A61K 8/23; A61K 8/20; A61K 8/42; A61K 8/4966; A61K 8/8182; A61K 8/19; A61K 2800/4324; A61Q 5/10; C11D 1/00
See application file for complete search history.

(56) References Cited

U.S. PATENT DOCUMENTS

| | | | |
|---|---|---|---|
| 4,370,142 A | 1/1983 | Bugaut et al. | |
| 4,425,132 A | 1/1984 | Grollier et al. | |
| 5,431,698 A * | 7/1995 | Tennigkeit ............. | A61K 8/411 8/406 |
| 6,916,343 B1 | 7/2005 | Akram et al. | |
| 2005/0000035 A1 * | 1/2005 | Chan ........................ | A61K 8/22 8/405 |

FOREIGN PATENT DOCUMENTS

| | | | |
|---|---|---|---|
| DE | 10037580 A1 * | 2/2002 | ............... A61K 7/13 |
| DE | 20100140 U1 | 6/2002 | |
| WO | 03/068177 A2 | 8/2003 | |

OTHER PUBLICATIONS

Foreign priority application No. 10 2014 216 942.9 (dated Aug. 26, 2014).*
PCT International Search Report (PCT/EP2015/068561) dated Jul. 9, 2015.

* cited by examiner

*Primary Examiner* — Eisa B Elhilo
(74) *Attorney, Agent, or Firm* — David K. Benson

(57) ABSTRACT

A method for the oxidative dyeing of keratinic fibers includes the following steps:
applying a cosmetic agent (M1) to the keratinic fibers,
allowing agent (M1) to act on the keratinic fibers for a time period of 30 seconds to 40 minutes at a temperature of at least 25° C.,
applying a cosmetic agent (M2) to the keratinic fibers treated with cosmetic agent (M1),
allowing cosmetic agents (M1) and (M2) to act on the keratinic fibers for a time period of 1 to 70 minutes, and
rinsing out of cosmetic agents (M1) and (M2).
Cosmetic agent (M1) includes
at least one oxidation dye precursor of the developer type (M1-1),
at least one oxidation dye precursor of the coupler type (M1-2),
at least one direct dye (M1-3), and
at least one surfactant (M1-4).
Cosmetic agent (M2) includes
at least one oxidation dye precursor (M2-1) and
at least one oxidizing agent (M2-2).

16 Claims, No Drawings

MULTI-TONAL ONE STEP DYEING WITH FOAM-TYPE PRE-TREATMENT SOLUTION

FIELD OF THE INVENTION

The present invention generally relates to a method for treating keratinic fibers, which makes it possible to color hair in one dyeing step and simultaneously to produce a multi-tonal coloring with lighter ("highlights") or darker ("lowlights") sections (streaks).

BACKGROUND OF THE INVENTION

Over time and particularly with exposure to external influences such as light or harmful atmospheric substances, the hair loses or changes its natural color and its shine or luster. For this reason, hair coloring agents are widely used either at hair salons or at home.

So-called oxidation dyes are used for permanent, intensive colors with suitable fastness properties. Such coloring agents typically contain oxidation dye precursors, so-called developer components and coupler components, which form the actual dyes with one another under the influence of oxidizing agents or atmospheric oxygen. The oxidation dyes are characterized by excellent, long-lasting coloring results. Coloring or tinting agents, containing so-called substantive dyes ("direct dyes") as the coloring component, are typically used for temporary colorings.

Apart from dyeing, the lightening of the natural hair color or dyeing the hair a blond color is the very specific wish of many consumers, because a blond hair color is regarded as attractive and fashionably desirable. If substrates are to be lightened or even bleached, the dyes coloring the substrate are mostly decolorized oxidatively with the use of appropriate oxidizing agents, such as hydrogen peroxide.

In hair dyeing, particularly in hair dyeing at home, the problem arises that natural color nuances are completely covered, so that multi-tonal colorings are difficult to realize.

So as to give the hair a natural appearance, it is known in the prior art to partially decolorize dyed hair by the selective use of oxidizing agents. The hair sections ("streaks") to which the oxidizing agents are applied thereby bleach out at least partially, resulting in a multi-tonal hair color. The oxidizing agent is applied thereby with a brush or applicator, wherein the hair not to be treated is optionally protected from decolorizing by aluminum foil or a so-called "highlighting cap."

This type of application does in fact solve the problem of the most possible natural coloring of hair, but allows only the placing of "highlights." The hair must be dyed again to achieve "lowlights," i.e., darker sections. In the previously described cases, therefore, a time-consuming second decolorizing or dyeing step would be necessary, which follows the first dyeing. In particular during use at home, therefore, the entire hair must first be colored, before the consumer can place "highlights" or "lowlights." Many consumers regard this as too time-consuming and also as frustrating, because the essential color-changing step occurs at the beginning and is only "corrected" in a second step.

It is therefore desirable to provide a method that enables multi-tonal coloring in one coloring step. In this regard, the coloring of the hair with the creation of "highlights" or "lowlights" should proceed so that a result is visible immediately after the coloring agent is rinsed out. Furthermore, it is desirable to create "highlights" or "lowlights" without smearing the streak result.

Furthermore, other desirable features and characteristics of the present invention will become apparent from the subsequent detailed description of the invention and the appended claims, taken in conjunction with this background of the invention.

BRIEF SUMMARY OF THE INVENTION

A method for the oxidative dyeing of keratinic fibers, wherein the method comprises the following process steps in the indicated sequence: a) applying a cosmetic agent (M1) to the keratinic fibers; b) allowing agent (M1) to act on the keratinic fibers for a time period of 30 seconds to 40 minutes at a temperature of at least 25° C.; c) applying a cosmetic agent (M2) to the keratinic fibers treated with cosmetic agent (M1); d) allowing cosmetic agents (M1) and (M2) to act on the keratinic fibers for a time period of 1 to 70 minutes; e) rinsing out of cosmetic agents (M1) and (M2), characterized in that cosmetic agent (M1) includes at least one oxidation dye precursor of the developer type (M1-1), includes at least one oxidation dye precursor of the coupler type (M1-2), includes at least one direct dye (M1-3), and includes at least one surfactant (M1-4); cosmetic agent (M2) includes at least one oxidation dye precursor (M2-1), and includes at least one oxidizing agent (M2-2).

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has now been found that a partial pretreatment of fiber areas or streaks has the result that this area or streaks are dyed more intensively or less intensively later. By prepenetrating or pretreating individual fiber areas or streaks, the coloring agent used immediately thereafter colors the hair multi-tonally, and a natural coloring result with "highlights" or "lowlights" is obtained immediately after the dying step. The drying of the prepenetration solution prevents smearing or running off of this solution to other hair sections and therefore also a smearing of the streak result.

The subject matter of the present invention is a method for the oxidative coloring of keratinic fibers, the method comprising the following steps in the indicated sequence:
a) applying a cosmetic agent (M1) to the keratinic fibers,
b) allowing agent (M1) to act on the keratinic fibers for a time period of 30 seconds to 40 minutes at a temperature of at least 25° C.,
c) applying a cosmetic agent (M2) to the keratinic fibers treated with cosmetic agent (M1),
d) allowing cosmetic agents (M1) and (M2) to act on the keratinic fibers for a time period of 1 to 70 minutes,
e) rinsing out cosmetic agents (M1) and (M2),
characterized in that
   cosmetic agent (M1)
      includes at least one oxidation dye precursor of the developer type (M1-1),
      includes at least one oxidation dye precursor of the coupler type (M1-2),
      includes at least one direct dye (M1-3), and
      includes at least one surfactant (M1-4), cosmetic agent (M2)
  includes at least one oxidation dye precursor (M2-1) and
  includes at least one oxidizing agent (M2-2).

The term "keratinic fibers or keratin fibers as well" is understood according to the invention to mean pelts, wool, feathers, and human hair. It is particularly preferred in the context of the present invention if the method of the invention is used for coloring human hair.

According to the invention, process steps a) to e) are preferably carried out in the previously given sequence with a time interval between the individual process steps of 0 to 60 minutes in each case, preferably of 0 to 40 minutes in each case, and in particular of 0 to 30 minutes in each case.

In the first step (process step a)) of the method of the invention, a cosmetic agent (M1) is applied to the fibers. Said cosmetic agent (M1), which is also called a pretreatment agent or a prepenetrating agent below, is left on the keratinic fibers for a period of 30 seconds to 40 minutes at a temperature of at least 25° C. (step b) of the method of the invention).

Shorter contact times of the pretreatment agent are preferred, however, according to the invention. Particularly preferred methods of the invention are therefore characterized in that cosmetic agent (M1) in process step b) is allowed to act on the keratinic fibers at a temperature of 25° C. to 120° C., in particular of 30° C. to 120° C., for a time period of 30 seconds to 35 minutes, primarily of 30 seconds to 30 minutes, preferably of 30 seconds to 20 minutes, in particular of 30 seconds to 15 minutes. The pretreatment of keratinic fibers with cosmetic agent (M1) has the result that at these places ingredients of pretreatment agent (M1) adhere to the keratinic fibers or have penetrated into the keratinic fibers, so that the coloring result in the case of a subsequent application of cosmetic agent (M2) is enhanced or lightened at these sites. The hair can be colored in one dyeing step in this way and a multi-tonal coloring with lighter ("highlights") or darker ("lowlights") sections (streaks) can be produced simultaneously. Because of the higher temperatures during the contact time of pretreatment agent (M1), which can be achieved, for example, by means of a hair dryer or a drying hood, a preferably complete drying of pretreatment agent (M1) on the keratinic fibers is achieved. This drying, on the one hand, prevents a smearing or running off of pretreatment agent (M1) during the subsequent application of cosmetic agent (M2) and, on the other, leads to a sufficient separation of streaks treated with pretreatment agent (M1). Smearing of the streak result is prevented in this way when the method of the invention is carried out.

To achieve multi-tonal colorings, cosmetic agent (M1) should not be applied evenly to the keratinic fibers. Preferably, only individual regions, especially preferably only individual streaks are treated with cosmetic agent (M1). Alternatively, the concentrations, applied to individual streaks, of cosmetic agent (M1) can be varied. It is also possible to apply cosmetic agent (M1) first evenly to all keratinic fibers and then to treat again individual areas or streaks with cosmetic agent (M1). A repeated treatment of individual regions/streaks with cosmetic agent (M1) is also possible according to the invention.

It is particularly preferred in this regard if cosmetic agent (M1) is applied only to individual streaks in process step a). The term "streaks" according to the invention is understood to mean a portion that is separated from the totality of keratinic fibers and consists of at least 2, preferably at least 50, in particular at least 100, keratinic fibers.

After the treatment time of the pretreatment agent, the keratinic fibers are not rinsed out or toweled off. Rather, in process step c) of the method of the invention, a cosmetic agent (M2) is applied to the keratinic fibers still being acted on by cosmetic agent (M1). The mixture of cosmetic agents (M1) and (M2), which forms by the application of agent (M2) to the keratinic fibers, is allowed to act for a time period from 1 to 70 minutes in process step d) of the method of the invention.

According to the invention, however, shorter contact times of cosmetic agents (M1) and (M2) in process step d) are preferable. Particularly preferred methods of the invention are characterized in that in process step d) cosmetic agents (M1) and (M2) are allowed to act for a time period from 1 to 60 minutes, preferably from 5 to 50 minutes, in particular from 10 to 45 minutes.

Because in step b) of the method of the invention cosmetic agent (M1) was already left for a certain time on the keratinic fibers, these keratinic fibers have a longer contact with the ingredients of cosmetic agent (M1) than with those of cosmetic agent (M2). If cosmetic agent (M1) was applied only to individual streaks or in individual areas, the ingredients of cosmetic agent (M1) could act more intensively in these regions and thus intensify or weaken the effect of the ingredients of cosmetic agent (M2) in these regions, as a result of which a darker and lighter coloring of these regions is achieved.

After cosmetic agents (M1) and (M2) are rinsed out in step e) of the method of the invention, without having to carry out another step, a multi-tonal coloring result is obtained directly.

Cosmetic agent (M1) or the pretreatment agent is an oxidative hair coloring agent, which includes at least one oxidation dye precursors of the developer type (M1-1). Preferred according to the invention is the at least one oxidation dye precursor of the developer type (M1-1) selected from the group comprising 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one, p-phenylenediamine, p-toluylenediamine, 2-(2-hydroxyethyl)-p-phenylenediamine, 2-(1,2-dihydroxyethyl)-p-phenylenediamine, N,N-bis(2-hydroxyethyl)-p-phenylenediamine, 2-methoxymethyl-p-phenylenediamine, N-(4-amino-3-methylphenyl)-N-[3-(1H-imidazol-1-yl)propyl]amine, bis(2-hydroxy-5-aminophenyl)methane, 1,3-bis(2,5-diaminophenoxy)propan-2-ol, N,N'-bis(4-aminophenyl)-1,4-diazacycloheptane, 1,10-bis(2,5-diaminophenyl)-1,4,7,10-tetraoxadecane, p-aminophenol, 4-amino-3-methylphenol, and the physiologically acceptable salts thereof and mixtures thereof.

To obtain natural colorings, typically a plurality of oxidation dye precursors of the developer type must be used. Preferred cosmetic agents (M1) are therefore characterized in that the at least one oxidation dye precursor of the developer type (M1-1) is selected from at least one of the following combinations: p-toluylenediamine/2-(2-hydroxyethyl)-p-phenylenediamine; p-toluylenediamine/2-methoxymethyl-p-phenylenediamine; p-toluylenediamine/N,N-bis(2-hydroxyethyl)-p-phenylenediamine; p-toluylenediamine/2-methoxymethyl-p-phenylenediamine; p-toluylenediamine/N-(4-amino-3-methylphenyl)-N-[3-(1H-imidazol-1-yl)propyl]amine; p-toluylenediamine/bis(2-hydroxy-5-aminophenyl)methane; p-toluylenediamine/4-amino-3-methylphenol; p-toluylenediamine/4,5-diamino-1-(2-hydroxyethyl)pyrazole; p-toluylenediamine/2,4,5,6-tetraaminopyrimidine; 2-(2-hydroxyethyl)-p-phenylenediamine/2-methoxymethyl-p-phenylenediamine; 2-(2-hydroxyethyl)-p-phenylenediamine/N,N-bis(2-hydroxyethyl)-p-phenylenediamine; 2-(2-hydroxyethyl)-p-phenylenediamine/2-methoxymethyl-p-phenylenediamine; 2-(2-hydroxyethyl)-p-phenylenediamine/N-(4-amino-3-methyl-phenyl)-N-[3-(1H-imidazol-1-yl)propyl]amine; 2-(2-hydroxyethyl)-p-phenylenediamine/bis(2-hydroxy-5-aminophenyl)methane; 2-(2-hydroxyethyl)-p-phenylenediamine/4-amino-3-methylphenol; 2-(2-hydroxyethyl)-p-phenylenediamine/4,5-diamino-1-(2-hydroxyethyl)pyrazole; 2-(2-hydroxyethyl)-p-phenylenediamine/2,4,5,6-tetraaminopyrimidine; 2-methoxymethyl-p-phenylenediamine/2-(2-hydroxyethyl)-p-phenylenediamine; 2-methoxymethyl-p-phenylenediamine/2-methoxymethyl-p-phenylenediamine; 2-methoxymethyl-p-phenylenediamine/N,N-bis(2-hydroxyethyl)-p-phenylenediamine; 2-methoxymethyl-p-phenylenediamine/2-methoxymethyl-p-phenylenediamine; 2-methoxymethyl-p-phenylenediamine/N-(4-amino-3-methylphenyl)-N-[3[(1H-imidazol-1-yl)propyl]amine; 2-methoxymethyl-p-phenylenediamine/bis(2-hydroxy-5-aminophenyl)methane; 2-methoxymethyl-p-phenylenediamine/4-amino-3-methylphenol; 2-methoxymethyl-p-phenylenediamine/4,5-diamino-1-(2-hydroxyethyl)pyrazole; 2-methoxymethyl-p-phenylenediamine/2,4,5,6-tetraaminopyrimidine, and/or 4- and amino-3-methylphenol/4,5-diamino-1-(2-hydroxyethyl)pyrazole, and/or the physiologically acceptable salts thereof.

According to a particularly preferred embodiment of the first subject of the invention, the at least one oxidation dye precursor of the developer type (M1-1) is selected from the group comprising p-toluylenediamine, 4-amino-3-methylphenol, 4,5-diamino-1-(2-hydroxyethyl)pyrazole, 2,4,5,6-tetraaminopyrimidine, and/or the physiologically acceptable salts thereof and mixtures thereof. It has emerged that the use of these special oxidation dye precursors of the developer type (M1-1) in pretreatment agents (M1) used in the context of the method of the invention leads to especially vibrant, colorfast, rub-resistant, sweat-resistant, and UV-resistant multi-tonal colors.

Especially attractive multi-tonal colorings are obtained, if cosmetic agent (M1) includes the at least one oxidation dye precursor of the developer type (M1-1) in a total amount of 0.0025 to 10.0% by weight, primarily of 0.004 to 8.0% by weight, preferably 0.005 to 5.0% by weight, in particular 0.01 to 3.5% by weight, based on the total weight of cosmetic agent (M1). The aforementioned amounts of the developer component (M1-1) lead to multi-tonal colorings, which have particularly intense and vivid colors and a high resistance to environmental influences, such as hair washing, UV light, sweat, and rubbing.

Pretreatment agent (M1) includes as a further component at least one oxidation dye precursor of the coupler type (M1-2). Oxidation dye precursors of the coupler type in the context of the oxidative dyeing alone form no significant coloring but require the presence of oxidation dye precursors of the developer type for a sufficient coloring. Oxidation dye precursors of the coupler type in the context of the invention permit at least one substitution of a chemical group of the coupler by the oxidized form of the developer component. In this regard, a covalent bond forms between the coupler and developer component.

In the context of the present invention, it is preferable if the at least one oxidation dye precursor of the coupler type (M1-2) is selected from the group comprising m-aminophenol and derivatives thereof, o-aminophenol and derivatives thereof, m-diaminobenzene and derivatives thereof, o-diaminobenzene and derivatives thereof, di- and trihydroxybenzene derivatives, pyridine derivatives, naphthalene derivatives, morpholine derivatives, quinoxaline derivatives, pyrazole derivatives, indole derivatives, pyrimidine derivatives, methylenedioxybenzene derivatives, and/or the physiologically acceptable salts thereof and mixtures thereof.

Preferred methods of the invention are characterized in that the at least one oxidation dye precursor of the coupler type (M1-2) is selected from the group comprising resorcinol, 2-methylresorcinol, 5-amino-2-methylphenol, 3-aminophenol, 2-(2,4-diaminophenoxy)ethanol, 1,3-bis(2,4-diaminophenoxy)propane, 1-methoxy-2-amino-4-(2'-hydroxyethylamino)benzene, 2-amino-3-hydroxypyridine, 2,6-dihydroxy-3,4-dimethylpyridine, 1,5-dihydroxynaphthalene, 2,7-dihydroxynaphthalene, 1-naphthol, and/or the physiologically acceptable salts thereof and mixtures thereof. The aforementioned coupler components (M1-2) in combination with the at least one developer component (M1-1) in pretreatment agents (M1) lead to especially intensive and lasting multi-tonal coloring results.

According to the invention, cosmetic agent (M1) preferably includes the at least one oxidation dye precursor of the coupler type (M1-2) in a total amount of 0.001 to 6.0% by weight, primarily of 0.001 to 5.5% by weight, preferably of 0.002 to 4.5% by weight, in particular of 0.005 to 2.5% by weight, based on the total weight of cosmetic agent (M1). The aforementioned amounts of coupler component (M1-2) in pretreatment agents (M1) used in the context of the method of the invention lead to especially vibrant, colorfast, rub-resistant, sweat-resistant, and UV-resistant multi-tonal colorings.

So as to assure a balanced and subtle nuance formation, pretreatment agents (M1) used in the context of the method of the invention contain at least one direct dye (M1-3). Direct dyes are dyes that are directly absorbed onto the hair and do not require any oxidative process to develop the color. Direct dyes are usually nitrophenylenediamines, nitroaminophenols, azo dyes, anthraquinones, or indophenols.

According to a preferred embodiment of the first subject of the invention, the at least one direct dye (M1-3) is selected from the group of anionic direct dyes, cationic direct dyes, nonionic direct dyes, and mixtures thereof.

In this regard, it can be provided according to the invention that the anionic direct dye is selected from the group comprising Acid Yellow 1, Acid Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, tetrabromophenol blue, and/or the physiologically acceptable salts thereof.

In the context of this embodiment, it can be provided further that the cationic direct dye is selected from the group comprising Basic Blue 7, Basic Blue 26, Basic Violet 2 and Basic Violet 14, Basic Yellow 57, Basic Red 76, Basic Blue 99, Basic Brown 16 and Basic Brown 17 and HC Blue 16, as well as Basic Yellow 87, Basic Orange 31 and Basic Red 51, and/or the physiologically acceptable salts thereof.

Moreover, it can also be provided in the context of this embodiment that the nonionic direct dye is selected from the group comprising HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, 1,4-diamino-2-nitrobenzene, 2-amino-4-nitrophenol, 1,4-bis(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene 2-[(4-amino-2-nitrophenyl)amino]benzoic acid, 6-nitro-1,2,3,4-tetrahydroquinoxaline, 2-hydroxy-1,4-naphthoquinone, picramic acid, 2-amino-6-chloro-4-nitrophenol, 4-ethylamino-3-nitrobenzoic acid, and 2-chloro-6-ethylamino-4-nitrophenol, and the physiologically acceptable salts thereof, preferably 2-amino-6-chloro-4-nitrophenol and/or 4-amino-3-nitrophenol, and/or the physiologically acceptable salts thereof.

In the context of the method of the invention, pretreatment agents (M1) used with particular preference contain at least one direct dye (M1-3), which is selected from the group of 2-amino-6-chloro-4-nitrophenol, HC Blue 12, HC Yellow 2, HC Violet 14D, and/or the physiologically acceptable salts thereof and mixtures thereof. When these special direct dyes are used, an especially balanced and subtle nuance formation is achieved during the method of the invention or in the multi-tonal coloring.

According to the invention, cosmetic agent (M1) preferably includes the at least one direct dye (M1-3) in a total amount of 0.0001 to 6.0% by weight, primarily of 0.0005 to 5.5% by weight, preferably of 0.0008 to 5.0% by weight, more preferably of 0.005 to 4.5% by weight, in particular of 0.001 to 3.5% by weight, based on the total weight of cosmetic agent (M1). The aforementioned amounts of the direct dyes lead to especially balanced nuances of the multi-tonal color ing according to the method of the invention.

Pretreatment agent (M1) used in the context of the method of the invention includes furthermore at least one surfactant (M1-4). Surfactants in the context of the present invention are amphiphilic (bifunctional) compounds, which consist of at least one hydrophobic and at least one hydrophilic moiety. A basic property of surfactants and emulsifiers is the oriented absorption on interfaces and the aggregation to form micelles and the formation of lyotrophic phases.

According to a preferred embodiment of the first subject of the invention, the at least one surfactant (M1-4) is selected from the group comprising nonionic surfactants, anionic surfactants, amphoteric surfactants, zwitterionic surfactants, cationic surfactants, and mixtures thereof.

In this regard, it can be provided according to the invention that the nonionic surfactant is selected from the group comprising ethoxylated alcohols and carboxylic acids having 8 to 13 carbon atoms and 2 to 30 ethylene oxide units, adducts of 5 to 60 mol of ethylene oxide to castor oil and hydrogenated castor oil, alkyl polyglucosides of the formula $R^1O$-$[G]_p$, where $R^1$ stands for an alkyl and/or alkenyl group having 4 to 22 carbon atoms, G for a sugar group having 5 or 6 carbon atoms, and p for numbers from 1 to 10, monoethanolamides of carboxylic acids having 8 to 30 carbon atoms, and mixtures thereof.

In the context of this embodiment, it can be provided, furthermore, that the anionic surfactant is selected from the group comprising alkyl sulfates and alkyl polyglycol ether sulfates of the formula $R^2$—$O(CH_2$—$CH_2O)_x$—$OSO_3H$, where $R^2$ is a linear alkyl group having 8 to 30 carbon atoms and x=0 or 1 to 12, salts of linear and branched carboxylic acids having 8 to 30 carbon atoms, ether carboxylic acids of the formula $R^3$—$O$—$(CH_2$—$CH_2O)_x$—$CH_2$—$COOH$, where $R^3$ is a linear alkyl group having 8 to 30 C atoms and x=0 or 1 to 16, and mixtures thereof.

Moreover, it can also be provided in the context of this embodiment that the amphoteric surfactant is selected from the group comprising amphoacetates with carboxylic acid esters having 8 to 30 carbon atoms, N-alkylglycines, N-alkylpropionic acids, N-alkylamidobutyric acids, N-alkyliminodipropionic acids, N-hydroxyethyl-N-alkylamidopropyl glycines, N-alkyltaurines, N-alkylsarcosines, 2-alkylaminopropionic acids, alkylaminoacetic acids, and mixtures thereof.

It can be provided in addition in the context of this embodiment that the zwitterionic surfactant is selected from the group comprising betaines, N-alkyl-N,N-dimethylammonium glycinates, N-acylamidopropyl-N,N-dimethylammonium glycinates, 2-alkyl-3-carboxymethyl-3-hydroxyethyl imidazolines, and mixtures thereof.

Pretreatment agents (M1) used particularly preferably in the context of the method of the invention contain at least one surfactant (M1-4), which is selected from the group comprising alkyl polyglucosides of the formula $R^1O$-$[G]_p$, where $R^1$ stands for an alkyl and/or alkenyl group having 4 to 22 carbon atoms, G for a sugar group having 5 or 6 carbon atoms, and p for numbers from 1 to 10, monoethanolamides of carboxylic acids having 8 to 30 carbon atoms, amphoacetates with carboxylic acid esters having 8 to 30 carbon atoms, and mixtures thereof. The use of the aforementioned surfactants leads to an especially good foam quality and therefore to high wetting of the keratinic fibers with pretreatment agent (M1). Furthermore, the use of these surfactants leads to a good distributability of pretreatment agents (M1) in process step a) and to a sufficient, particularly complete, drying of pretreatment agents (M1) during the contact time in process step b). Because of the drying of pretreatment agent (M1) on the keratinic fibers, smearing during application of cosmetic agent (M2) in process step c) and therefore also smearing of the multi-tonal coloring result are prevented.

Preferably according to the invention, cosmetic agent (M1) includes the at least one surfactant (M1-4) in a total amount of 0.1 to 30% by weight, primarily of 0.5 to 20% by weight, preferably of 1.0 to 15% by weight, more preferably of 3.0 to 13% by weight, in particular of 4.0 to 12% by weight, based on the total weight of cosmetic agent (M1). The aforementioned amounts of the surfactants assure a good foam quality and a sufficiently rapid drying of pretreatment agent (M1) in process step b) of the method of the invention.

A specific viscosity of the agent has proven advantageous to be able to apply prepenetrating agent (M1) in a clean and locally limited manner. It is advantageous to this end, if the agent is not a paste, viscous cream, or thickened gel, but has a sufficient flowability. Furthermore, cosmetic agent (M1) must in fact have rheological properties that allow application to the fibers to be dyed, but simultaneously also prevent the running off or flowing away of cosmetic agent (M1) from the keratinic fibers, in particular under the action of heat, during the contact time in process step b). Cosmetic agents (M1) used preferably according to the invention therefore have a dynamic viscosity of 10 to 300 mPa*s, primarily of 20 to 200 mPa*s, preferably of 30 to 100 mPa*s, more preferably of 40 to 90 mPa*s, in particular of 50 to 80 mPa*s, in each case measured using a Brookfield RDV II+, spindle No. 1, 100 rpm, 20° C.

In the context of a particularly preferred embodiment of the first subject of the invention, cosmetic agent (M1) is present as a foam and has a liquid separation after 10 minutes of 0.0 to 60%, primarily of 0.0 to 50%, in particular of 0.0 to 40%. Pretreatment agents (M1), which are present as a foam and have the aforementioned liquid separation, on the one hand, permit complete wetting of keratinic fibers treated with said agent. On the other hand, this consistency assures a sufficient, in particular complete, drying of the foam-type pretreatment agent (M1) by heat in process step b). This preferably complete drying of pretreatment agent (M1) prevents smearing of said agent during application of cosmetic agent (M2) and therefore smearing of the multitonal coloring result.

The liquid separation of cosmetic agent (M1) after 10 minutes can be determined, for example, by the following measuring method: First, the weight of a specific volume, for example, 80 mL, of the foam-like cosmetic agent (M1) is determined (reference value). After 10 minutes, the separated liquid is decanted and the weight of this liquid is determined. The liquid separation is calculated as a % using the following formula: liquid separation after 10 minutes= [weight of liquid (g)/weight of agent (M1) (g)]*100

Pretreatment agents (M1) used in the context of the method of the invention can be produced as a propellant-free cosmetic agent or as a propellant-containing cosmetic agent. Propellant-free cosmetic agents (M1) can be discharged in any propellant gas-free spray system, which has a dispensing container and a spray valve, therefore, e.g., in a flexible pressure bottle with an immersion tube and spray valve (squeeze bottle) or in a pump spray bottle, the pump lever of which is actuated with the index finger or with the entire hand in the manner of a trigger guard.

If pretreatment agents (M1) are produced as propellant-containing cosmetic agents, they contain in addition at least one propellant. In the context of this embodiment, cosmetic agent (M1) includes at least one propellant, selected from the group of $N_2O$, dimethyl ether, $CO_2$, air, propane, n-butane, isobutane, n-pentane, isopentane, and mixtures thereof, preferably a mixture of propane and n-butane in the weight ratio of 15:85.

In the context of this embodiment, it is preferable further if cosmetic agent (M1) includes the at least one propellant in a total amount of 0.5 to 16% by weight, primarily of 1.0 to 14% by weight, preferably of 3.0 to 13% by weight, more preferably of 4.0 to 12% by weight, in particular of 5.5 to 10% by weight, based on the total weight of cosmetic agent (M1).

In addition to the oxidation dye precursor(s) of the developer type and coupler type, the direct dye(s), and the surfactant(s), cosmetic agent (M1) used in the method of the invention can contain other ingredients.

According to the invention, cosmetic agent (M1) preferably includes in addition at least one other compound, selected from the group comprising (i) thickeners; (ii) linear or branched, saturated or unsaturated alcohols having 8 to 20 carbon atoms; (iii) alkalizing agents; and (iv) mixtures thereof.

So as to establish the desired viscosity, cosmetic agents (M1) can contain at least one thickener and/or at least one gelling agent.

In this regard, it can be provided, therefore, that cosmetic agents (M1) contain at least one anionic, polymeric thickener. Preferred anionic polymeric thickeners are selected from crosslinked or non-crosslinked copolymers that contain at least two different monomers from the group comprising acrylic acid, methacrylic acid, $C_1$-$C_6$ alkyl esters of acrylic acid, and/or $C_1$-$C_6$ alkyl esters of methacrylic acid. Particularly preferred anionic copolymers are copolymers of acrylic acid, methacrylic acid, or the $C_1$-$C_6$ alkyl esters thereof, which are marketed under the INCI name of Acrylates Copolymer. Preferred in particular is the combination of methacrylic acid and ethyl acrylate and optionally crosslinked, multifunctional monomers. A preferred commercial product for this is, for example, Aculyn® 33 or 33A, which is sold by the company Rohm & Haas.

The anionic polymeric thickeners can be used in a total amount of 0.1 to 15% by weight, preferably of 1 to 10% by weight, in particular of 1.5 to 7.5% by weight, based on the total weight of cosmetic agent (M1).

Pretreatment agents (M1) used according to the invention in process step b) can also contain linear or branched, saturated or unsaturated alcohols having 8 to 20 carbon atoms. It emerged that the additional presence of these higher-chain alcohols can improve even further the multitonal coloring result of the method of the invention. It is preferred, therefore, if pretreatment agents (M1) used in the method of the invention contain in addition one or more alcohols from the group comprising arachidyl alcohol (eisocan-1-ol), gadoleyl alcohol ((9Z)-eicos-9-en-1-ol), arachidonyl alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and brassidyl alcohol ((13E)-docosen-1-ol).

Especially suitable cosmetic agents (M1) contain one or more higher-chain alcohols of the aforementioned group in a total amount of 1.0 to 10.0% by weight, primarily of 1.4 to 8.0% by weight, preferably of 1.8 to 6.0% by weight, in particular of 2.0 to 4.0% by weight, based on the total weight of cosmetic agent (M1).

In a further preferred embodiment, a cosmetic agent (M1) used in the method of the invention is therefore characterized in that it includes in addition one or more alcohols from the group comprising arachidyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and brassidyl alcohol ((13E)-docosen-1-ol) in a total amount of 0.1 to 10.0% by weight, primarily of 1.4 to 8.0% by weight, preferably of 1.8 to 6.0% by weight, in particular of 2.0 to 4.0% by weight, based on the total weight of cosmetic agent (M1).

Pretreatment agents (M1) used in the context of the method of the invention can also contain at least one alkalizing agent.

Organic alkalinizing agents that can be used according to the invention are preferably selected from alkanolamines of primary, secondary, or tertiary amines with a $C_2$-$C_6$ alkyl parent structure, bearing at least one hydroxyl group. Very especially preferred alkanolamines according to the invention are selected from the group of 2-aminoethan-1-ol (monoethanolamine), 2-amino-2-methylpropan-1-ol, and 2-amino-2-methylpropane-1,3-diol, and mixtures thereof. An especially preferred alkanolamine is monoethanolamine. Suitable basic amino acids are lysine, arginine, and ornithine. Inorganic alkalinizing agents of the invention are preferably selected from the group comprising sodium hydroxide, potassium hydroxide, calcium hydroxide, barium hydroxide, sodium phosphate, potassium phosphate, sodium silicate, potassium silicate, sodium carbonate, and potassium carbonate, and mixtures thereof.

Methods especially preferred according to the invention are characterized in that cosmetic agent (M1) includes one or more alkalinizing agents from the group comprising sodium hydroxide, potassium hydroxide, ammonia, monoethanolamine, and 2-amino-2-methylpropanol in a total amount from 0.05 to 8.0% by weight, preferably of 0.1 to 6.0% by weight, in particular of 0.5 to 5.0% by weight, based on the total weight of cosmetic agent (M1).

Pretreatment agents (M1) used in the context of the method of the invention normally have a basic pH, in particular between pH 7.0 and pH 14. These pH values are necessary to assure an opening of the outer cuticle layer (cuticle) and to enable penetration of the oxidation dye precursors into the hair.

Methods preferred according to the invention are therefore characterized in that cosmetic agent (M1) has a pH value of pH 7.0 to pH 14.0, primarily of pH 8.8 to pH 11.0, preferably of pH 9.0 to pH 10.8, in particular of pH 9.2 to pH 10.5. The establishing of this pH can occur preferably with use of the aforementioned alkalizing agents.

In order to allow the natural and multi-tonal color result to emerge especially noticeably and surprisingly at the end of the method according to the invention, pretreatment agent (M1) is preferably not capable of being used by itself as a separate bleaching, lightening, or coloring agent. It is of particular advantage for this purpose, if cosmetic agents (M1) are free of oxidizing agents, in particular are free of hydrogen peroxide and/or persulfates.

The term "free of" in this case in the context of the present invention means that cosmetic agents (M1) contain no intentionally added oxidizing agents. Nevertheless, traces of these oxidizing agents can be introduced into cosmetic agents (M1) as contaminants or as minor components via other raw materials. "Free of" therefore more specifically means that cosmetic agents (M1) contain less than 1% by weight, primarily less than 0.5% by weight, preferably less than 0.25% by weight, more preferably less than 0.1% by weight, in particular less than 0.01% by weight, based on the total weight of cosmetic agent (M1), of oxidizing agents.

Methods preferred according to the invention are therefore characterized in that cosmetic agent (M1) used in process step a) includes less than 1% by weight, primarily less than 0.5% by weight, preferably less than 0.25% by weight, more preferably less than 0.1% by weight, in particular less than 0.01% by weight, based on the total weight of cosmetic agent (M1), of peroxo compounds. Peroxo compounds in the context of the present invention are understood to be compounds that contain at least one peroxide anion $O_2^{2-}$ or at least one peroxy group —O—O—.

Methods particularly preferred according to the invention are characterized in that cosmetic agents (M1) used in process step a) contain less than 1% by weight, primarily less than 0.5% by weight, preferably less than 0.25% by weight, more preferably less than 0.1% by weight, in particular less than 0.01% by weight, based on the total weight of cosmetic agent (M1), of hydrogen peroxide.

In process step c) of the method according to the invention, a cosmetic agent (M2) is applied to the keratinic fibers, still being acted upon by agent (M1). Said cosmetic agent (M2), which is also called a coloring agent hereafter, includes at least one oxidation dye precursor (M2-1) and at least one oxidizing agent (M2-2).

Preferred cosmetic agents (M2) contain at least one oxidation dye precursor of the developer and/or coupler type. Corresponding methods of the invention, in which cosmetic agent (M2) includes as an oxidation dye precursor (M2-1) one or more oxidation dye precursors of the developer type, are preferred according to the invention.

Suitable and preferred oxidation dye precursors of the developer type were already described further in detail above. The corresponding compounds can also be used in coloring agents (M2). It has emerged, however, that the use of certain oxidation dye precursors of the developer type in certain amounts in coloring agents (M2) is very suitable for producing especially vibrant, colorfast, rub-resistant, sweat-resistant, and UV-resistant multi-tonal colorings.

Particularly preferred methods of the invention are characterized in that cosmetic agent (M2) includes as an oxidation dye precursor of the developer type one or more compounds from the group comprising p-phenylenediamine, p-toluylenediamine, 2-(2-hydroxyethyl)-p-phenylenediamine, 2-(1,2-dihydroxyethyl)-p-phenylenediamine, N,N-bis(2-hydroxyethyl)-p-phenylenediamine, 2-methoxymethyl-p-phenylenediamine, N-(4-amino-3-methylphenyl)-N-[3-(1H-imidazol-1-yl)propyl]amine, and/or the physiologically acceptable salts thereof in a total amount of 0.0005 to 3.0% by weight, primarily of 0.001 to 2.75% by weight, preferably of 0.0025 to 2.5% by weight, in particular of 0.005 to 2.0% by weight, based on the total weight of cosmetic agent (M2).

Further especially preferred methods of the invention are characterized in that cosmetic agent (M2) includes as an oxidation dye precursor of the developer type one or more compounds from the group comprising bis(2-hydroxy-5-aminophenyl)methane, 1,3-bis(2,5-diaminophenoxy)propan-2-ol, N,N'-bis(4-aminophenyl)-1,4-diazacycloheptane, 1,10-bis(2,5-diaminophenyl)-1,4,7,10-tetraoxadecane, p-aminophenol, 4- and amino-3-methylphenol, and/or the physiologically acceptable salts thereof in a total amount of 0.0005 to 3.0% by weight, primarily of 0.001 to 2.75% by weight, preferably of 0.0025 to 2.5% by weight, in particular of 0.005 to 2.0% by weight, based on the total weight of cosmetic agent (M2).

Further particularly preferred methods of the invention are characterized in that cosmetic agent (M2) includes as an oxidation dye precursor of the developer type one or more compounds from the group comprising 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one, and/or the physiologically acceptable salts thereof in a total amount from 0.1 to 3.5% by weight, primarily of 0.3 to 2.8% by weight, preferably of 0.4 to 2.1% by weight, in particular of 0.5 to 1.6% by weight, based on the total weight of cosmetic agent (M2).

Further particularly preferred methods of the invention are characterized in that cosmetic agent (M2) includes as oxidation dye precursors of the developer type at least one of the following combinations: p-toluylenediamine/2-(2-hydroxyethyl)-p-phenylenediamine; p-toluylenediamine/2-methoxymethyl-p-phenylenediamine; p-toluylenediamine/N,N-bis(2-hydroxyethyl)-p-phenylenediamine; p-toluylenediamine/2-methoxymethyl-p-phenylenediamine; p-toluylenediamine/N-(4-amino-3-methylphenyl)-N-[3-(1H-imidazol-1-yl)propyl]amine; p-toluylenediamine/bis(2-hydroxy-5-aminophenyl)methane; p-toluylenediamine/4- and amino-3-methylphenol; p-toluylenediamine/4,5-diamino-1-(2-hydroxyethyl)pyrazole; p-toluylenediamine/2,4,5,6-tetraaminopyrimidine; 2-(2-hydroxyethyl)-p-phenylenediamine/2-methoxymethyl-p-phenylenediamine; 2-(2-hydroxyethyl)-p-phenylenediamine/N,N-bis(2-hydroxyethyl)-p-phenylenediamine; 2-(2-hydroxyethyl)-p-phenylenediamine/2-methoxymethyl-p-phenylenediamine; 2-(2-hydroxyethyl)-p-phenylenediamine/N-(4-amino-3-methyl-phenyl)-N-[3-(1H-imidazol-1-yl)propyl]amine; 2-(2-hydroxyethyl)-p-phenylenediamine/bis(2-hydroxy-5-aminophenyl)methane; 2-(2-hydroxyethyl)-p-phenylenediamine/4-amino-3-methylphenol; 2-(2-hydroxyethyl)-p-phenylenediamine/4,5-diamino-1-(2-hydroxyethyl)pyrazole; 2-(2-hydroxyethyl)-p- phenylenediamine/2,4,5,6-tetraaminopyrimidine; 2-methoxymethyl-p-phenylenediamine/2-(2-hydroxyethyl)-p-phenylenediamine; 2-methoxymethyl-p-phenylenediamine/2-methoxymethyl-p-phenylenediamine; 2-methoxymethyl-p-phenylenediamine/N,N-bis(2-hydroxyethyl)-p-phenylenediamine; 2-methoxymethyl-p-phenylenediamine/2-methoxymethyl-p-phenylenediamine; 2-methoxymethyl-p-phenylenediamine/N-(4-amino-3-methylphenyl)-N-[3 [(1H-imidazol-1-yl)propyl]amine; 2-methoxymethyl-p-phenylenediamine/bis(2-hydroxy-5-aminophenyl)methane; 2-methoxymethyl-p-phenylenediamine/4-amino-3-methylphenol; 2-methoxymethyl-p-phenylenediamine/4,5-diamino-1-(2-hydroxyethyl)pyrazole; 2-methoxymethyl-p-phenylenediamine/2,4,5,6-tetraaminopyrimidine, and/or 4- and amino-3-methylphenol/4,5-diamino-1-(2-hydroxyethyl) pyrazole, and/or the physiologically acceptable salts thereof.

According to the invention, cosmetic agent (M2) furthermore preferably includes one or more oxidation dye precursors of the coupler type.

Coupler components preferably used according to the invention are selected from one of the following classes: m-aminophenol, o-aminophenol, m-diaminobenzene, o-diaminobenzene, and/or derivatives thereof; naphthalene derivatives with at least one hydroxy group; di- or trihydroxybenzene; pyridine derivatives; pyrimidine derivatives; certain indole derivatives and indoline derivatives; pyrazolone derivatives (for example, 1-phenyl-3-methylpyrazol-5-one); morpholine derivatives (for example, 6-hydroxybenzomorpholine or 6-aminobenzomorpholine); quinoxaline derivatives (for example, 6-methyl-1,2,3,4-tetrahydroquinoxaline), and mixtures of two or more compounds of one or more of these classes.

Preferred m-aminophenol coupler components are selected from at least one compound from the group, comprising 3-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-(diethylamino)phenol, N-cyclopentyl-3-aminophenol, 1,3-dihydroxy-5-(methylamino)benzene, 3-ethylamino-4-methylphenol, 2,4-dichloro-3-aminophenol, and the physiologically acceptable salts thereof. Preferred m-diaminobenzene coupler components are selected from at least one compound from the group comprising m-phenylenediamine, 2-(2,4-diaminophenoxy)ethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)-amino]ethanol, 3-amino-4-(2-methoxyethoxy)-5-methylphenylamine, 1-amino-3-bis(2'-hydroxyethyl)aminobenzene, and the physiologically acceptable salts thereof. Preferred o-diaminobenzene coupler components are selected from at least one compound from the group comprising 3,4-diaminobenzoic acid and 2,3-diamino-1-methylbenzene, and the physiologically acceptable salts thereof. Preferred naphthalene derivatives with at least one hydroxy group are selected from at least one compound from the group comprising 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene, and 2,3-dihydroxynaphthalene. Preferred di- or trihydroxybenzenes and derivatives thereof are selected from at least one compound from the group comprising resorcinol, resorcinol monomethyl ether, 2-methylresorcinol, 5-methylresorcinol, 2,5-dimethylresorcinol, 2-chlororesorcinol, 4-chlororesorcinol, pyrogallol, and 1,2,4-trihydroxybenzene. Preferred pyridine derivatives are selected from at least one compound from the group comprising 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 3,4-diaminopyridine, 2-(2-methoxyethyl)amino-3-amino-6-methoxypyridine, 2-(4'-methoxyphenyl)amino-3-aminopyridine, and the physiologically acceptable salts thereof. Preferred pyrimidine derivatives are selected from at least one compound from the group comprising 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine, and 4,6-dihydroxy-2-methylpyrimidine, and the physiologically acceptable salts thereof. Preferred indole derivatives are selected from at least one compound from the group comprising 4-hydroxyindole, 6-hydroxyindole, and 7-hydroxyindole, and the physiologically acceptable salts thereof. Preferred indoline derivatives are selected from at least one compound from the group comprising 4-hydroxyindoline, 6-hydroxyindoline, and 7-hydroxyindoline, and the physiologically acceptable salts thereof.

Coupler components used particularly preferably according to the invention are selected from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxy ethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or mixtures of said compounds or the physiologically acceptable salts thereof. Very particularly preferred are resorcinol, 2-methylresorcinol, 5-amino-2-methylphenol, 3-aminophenol, 2-(2,4-diaminophenoxy)ethanol, 1,3-bis(2,4-diaminophenoxy)propane, 1-methoxy-2-amino-4-(2'-hydroxyethylamino)benzene, 2-amino-3-hydroxypyridine, and 1-naphthol, and one of the physiologically acceptable salts thereof.

Cosmetic agent (M2) preferably includes the coupler components in a total amount of 0.0001 to 2.0% by weight, in particular of 0.001 to 1.25% by weight, based on the total weight of cosmetic agent (M2).

The use of certain oxidation dye precursors of the coupler type in certain amounts in coloring agents (M2) results in multi-tonal colorings, which have especially vibrant, color-fast, rub-resistant, sweat-resistant, and UV-resistant multi-tonal colors.

Methods preferred according to the invention are therefore characterized in that cosmetic agent (M2) includes as an oxidation dye precursor of the coupler type one or more compounds from the group comprising 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, and/or the physiologically acceptable salt thereof in a total amount of 0.001 to 2.0% by weight, primarily of 0.0025 to 1.75% by weight, preferably of 0.0025 to 1.5% by weight, in particular of 0.005 to 1.25% by weight, based on the total weight of cosmetic agent (M2).

Further methods preferred according to the invention are characterized in that cosmetic agent (M2) includes as an oxidation dye precursor of the coupler type one or more compounds from the group comprising 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, and/or the physiologically acceptable salts thereof in a total amount of 0.001 to 2.0% by weight, primarily of 0.0025 to 1.75% by weight, preferably of 0.0025 to 1.5% by weight, in particular of 0.005 to 1.25% by weight, based on the total weight of cosmetic agent (M2).

Further methods preferred according to the invention are characterized in that cosmetic agent (M2) includes as an oxidation dye precursor of the coupler type one or more compounds from the group comprising resorcinol, 2-methylresorcinol, and/or 4-chlororesorcinol in a total amount of 0.001 to 2.0% by weight, primarily of 0.0025 to 1.75% by weight, preferably of 0.0025 to 1.5% by weight, in particular of 0.005 to 1.25% by weight, based on the total weight of cosmetic agent (M2).

Further methods preferred according to the invention are characterized in that cosmetic agent (M2) includes as an oxidation dye precursor of the coupler type one or more compounds from the group comprising 2-amino-3-hydroxypyridine, 3-amino-2-methyl amino-6-methoxypyridine, 2,6-dihydroxy-3,4-dimethylpyridine, 3,5-diamino-2,6-dimethoxypyridine, 1-phenyl-3-methylpyrazol-5-one, and/or the physiologically acceptable salts thereof in a total amount of 0.001 to 2.0% by weight, primarily of 0.0025 to 1.75% by weight, preferably of 0.0025 to 1.5% by weight, in particular of 0.005 to 1.25% by weight, based on the total weight of cosmetic agent (M2).

Further preferred methods according to the invention are characterized in that cosmetic agent (M2) includes as an oxidation dye precursor of the coupler type at least one of the following combinations: resorcinol/3-aminophenol; 2-methylresorcinol/3-aminophenol; 4-chlororesorcinol/3-aminophenol; resorcinol/5-amino-2-methylphenol; 2-methylresorcinol/5-amino-2-methylphenol; 4-chlororesorcinol/5-amino-2-methylphenol; resorcinol/2-hydroxy-4-aminophenoxyethanol; 2-methylresorcinol/2-hydroxy-4-aminophenoxyethanol; 4-chlororesorcinol/2-hydroxy-4-aminophenoxyethanol; resorcinol/2-amino-3-hydroxypyridine; 2-methylresorcinol/2-amino-3-hydroxypyridines; 4-chlororesorcinol/2-amino-3-hydroxypyridines; resorcinol/3-amino-2-methylamino-6-methoxypyridine; 2-methylresorcinol/3-amino-2-methylamino-6-methoxypyridine; 4-chlororesorcinol/3-amino-2-methylamino-6-methoxypyridine; resorcinol/2,6-dihydroxy-3,4-dimethylpyridine; 2-methylresorcinol/2,6-dihydroxy-3,4-dimethylpyridine, and/or 4-chlororesorcinol/2,6-dihydroxy-3,4-dimethylpyridine, and/or the physiologically acceptable salts thereof.

Pretreatment agent (M1) preferably includes oxidation dye precursors of the developer type (M1-1) in a higher total amount than cosmetic agent (M2) includes oxidation dye precursors (M2-1). This results in especially intense and vibrant multi-tonal colorings, which moreover have a high resistance to environmental influences such as, for example, hair washing, sweating, UV light, or rubbing.

According to a particularly preferred embodiment of the present invention, the molar ratio of the total quantity of all oxidation dye precursors of the developer type (M1-1) in cosmetic agent (M1) to the total amount of all oxidation dye precursors (M2-1) in cosmetic agent (M2) has a value (M1-1)/(M2-1) of 1:5 to 1:2, primarily of 1:1 to 2:1, preferably of 80:1 to 120:1, more preferably of 180:1 to 250:1, in particular of 400:1 to 600:1. The total amount in this case is understood to be the sum of the quantities of all oxidation dye precursors of the developer type (M1-1) used in cosmetic agent (M1) or the sum of the quantities of all oxidation dye precursors (M2-1) contained in cosmetic agent (M2).

A variation of the nuancing of the multi-tonal coloring is possible by a suitable selection of the oxidation dye precursors used in cosmetic agents (M1) and (M2). For a very naturally acting multi-tonal coloring with soft transitions, methods of the invention are preferred in which cosmetic agents (M1) and (M2) contain identical oxidation dye precursors of the developer type and of the coupler type.

If greater contrasts are desired, which are manifested in a more vibrant multi-tonal color appearance, methods of the invention have proven effective in which cosmetic agents (M1) and (M2) contain different oxidation dye precursors of the developer type.

It can be provided in the context of the method of the invention that cosmetic agents (M1) and (M2) contain identical ingredients. Preferably, however, cosmetic agents (M1) and (M2) differ in at least one ingredient.

Coloring agent (M2) can contain in addition direct dyes so as to assure a balanced nuancing of the multi-tonal colorings. According to a preferred embodiment of the subject of the invention, cosmetic agent (M2) includes in addition at least one direct dye from the group of anionic direct dyes, cationic direct dyes, nonionic direct dyes, and mixtures thereof.

Suitable and preferred direct dyes were already described in detail in regard to pretreatment agents (M1). The corresponding compounds can also be used in coloring agents (M2). It has emerged, however, that the use of certain direct dyes in certain amounts in coloring agents (M2) is especially highly suitable, because in this case an especially balanced nuancing of the multi-tonal colorings can be assured.

Cosmetic agents (M2) used with particular preference in the context of an embodiment of the method of the invention, therefore, contain in addition at least one direct dye, which is selected from the group comprising 2-amino-6-chloro-4-nitrophenol, HC Blue 12, HC Yellow 2, HC Violet 14D, and/or the physiologically acceptable salts thereof and mixtures thereof.

Methods of the invention in the context of this embodiment are characterized in that cosmetic agent (M2) includes the at least one direct dye in a total amount of 0.00001 to 5.0% by weight, primarily of 0.000025 to 4.0% by weight, preferably of 0.00005 to 3.0% by weight, more preferably of 0.0001 to 2.0% by weight, in particular of 0.0005 to 1.5% by weight, based on the total weight of cosmetic agent (M2).

Coloring agents (M2) furthermore can contain additional active substances, auxiliary substances, and additives in order to improve the coloring performance and to establish other desired properties of cosmetic agents (M2).

Preferably according to the invention, cosmetic agent (M2) therefore includes in addition at least one other compound, selected from the group comprising (i) thickeners; (ii) linear or branched, saturated or unsaturated alcohols having 8 to 20 carbon atoms; (iii) surfactants; (iv) alkalizing agents; and (v) mixtures thereof.

It has proven advantageous, if cosmetic agents (M2) also contain at least one thickener. There are no restrictions in principle with regard to these thickeners. Suitable thickeners are the compounds listed in regard to pretreatment agents (M1), which can also be used for thickening coloring agents (M2). In addition, the organic and inorganic thickeners listed below can also be used.

Suitable thickeners are anionic, synthetic polymers; cationic, synthetic polymers; naturally occurring thickeners, such as nonionic guar gums, scleroglucan gums or xanthan gums, gum arabic, gum ghatti, karaya gum, tragacanth gum, carrageenan gum, agar-agar, locust bean flour, pectins, alginates, starch fractions and derivatives such as amylose, amylopectin, and dextrins, as well as cellulose derivatives such as, for example, methylcellulose, carboxyalkylcelluloses, and hydroxyalkylcelluloses; nonionic, synthetic polymers such polyvinyl alcohol or polyvinylpyrrolidone; as well as inorganic thickeners, in particular phyllosilicates such as, for example, bentonite, in particular smectites, such as montmorillonite or hectorite.

Cosmetic agents (M2) used in the method of the invention can contain as thickeners zwitterionic polymers as well, which are selected from the group comprising
  copolymers of dimethyldiallylammonium salts and acrylic acid, e.g., Polyquaternium-22,
  copolymers of dimethyldiallylammonium salts and methacrylic acid,
  copolymers of N,N,N-trimethyl-3-[(2-methyl-1-oxo-2-propen-1-yl)amino]-1-propanaminium salts and acrylic acid,
  copolymers of N,N,N-trimethyl-3-[(2-methyl-1-oxo-2-propen-1-yl)amino]-1-propanaminium salts and methacrylic acid,
  copolymers of N,N,N-trimethyl-2-[(2-methyl-1-oxo-2-propen-1-yl)amino]-1-ethanaminium salts and acrylic acid,
  copolymers of N,N,N-trimethyl-2-[(2-methyl-1-oxo-2-propen-1-yl)amino]-1-ethanaminium salts and methacrylic acid,
  copolymers of N,N,N-trimethyl-3-[(2-methyl-1-oxo-2-propen-1-yl)amino]-1-propanaminium salts, acrylic acid, and acrylamide, e.g., Polyquaternium-53,
  copolymers of N,N,N-trimethyl-3-[(2-methyl-1-oxo-2-propen-1-yl)amino]-1-propanaminium salts, methacrylic acid, and acrylamide,
  copolymers of 1-ethenyl-3-methyl-1H-imidazolium salts, 1-ethenyl-1H-imidazole, 1-ethenyl-2-pyrrolidinone, and methacrylic acid, e.g., Polyquaternium-86,
  copolymers of 1-ethenyl-3-methyl-1H-imidazolium salts, 1-ethenyl-1H-imidazole, 1-ethenyl-2-pyrrolidinone, and acrylic acid.
Mixtures of the aforementioned zwitterionic polymers as well can be used for thickening cosmetic agents (M2).

Coloring agents (M2) used in the method of the invention can also contain the alcohols, described in regard to pretreatment agent (M1), from the group comprising arachidyl alcohol (eisocan-2-ol), gadoleyl alcohol ((9Z)-eicos-9-en-1-ol), arachidonyl alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and brassidyl alcohol ((13E)-docosen-1-ol) in a total amount of 0.1 to 10.0% by weight, primarily of 1.4 to 8.5% by weight, preferably from 1.8 to 8.0% by weight, in particular of 2.0 to 7.0% by weight, based on the total weight of cosmetic agent (M2).

Coloring agents (M2) are preferably provided as a liquid preparation and a surface-active substance is therefore added in addition to the agents, wherein such surface-active substances are called surfactants or emulsifiers depending on the field of application: they are preferably selected from anionic, cationic, zwitterionic, amphoteric, and nonionic surfactants and emulsifiers. The surfactants and emulsifiers that can be used in coloring agents (M2) have already been described in regard to pretreatment agents (M1).

It is preferred in the context of this embodiment, if the anionic surfactants in cosmetic agents (M2) are used in a total amount of 0.1 to 45% by weight, primarily of 1 to 30% by weight, in particular of 1 to 15% by weight, based on the total amount of cosmetic agent (M2).

Moreover, it is preferred in the context of this embodiment, if the nonionic and/or zwitterionic and/or amphoteric surfactants are used in a total amount of 0.1 to 45% by weight, primarily of 1 to 30% by weight, in particular of 1 to 15% by weight, based on the total amount of cosmetic agent (M2).

Cosmetic agent (M2) can also contain at least one alkalizing agent. Suitable alkalizing agents and their usable total amounts have already been given in regard to pretreatment agents (M1). The establishing of a basic pH with use of the at least one alkalizing agent is necessary to assure an opening of the outer cuticle layer (cuticle) and to enable penetration of the oxidation dye precursors into the hair.

Methods preferred according to the invention are therefore characterized in that cosmetic agent (M2) has a pH of pH 7.0 to pH 14.0, primarily of pH 8.8 to pH 11.0, preferably of pH 9.0 to pH 10.8, in particular of pH 9.2 to pH 10.5.

In order to achieve a vibrant multi-tonal coloring, it is advantageous if there are no great variations in pH during the sequential application of cosmetic agents (M1) and (M2), because only insufficient penetration of the keratinic fibers and thereby also a poorer coloring result can occur as a result. Methods of the invention are therefore preferred in which cosmetic agent (M1) and cosmetic agent (M2) have identical pH values.

The oxidation dye precursors (developer and coupler) themselves are not colored. The formation of the actual dyes occurs only during use by contact of the oxidation dye precursors with an oxidizing agent (primarily hydrogen peroxide). In a chemical reaction, the developers used as oxidation dye precursors (such as, for example, p-phenylenediamine derivatives or p-aminophenol derivatives) are converted by hydrogen peroxide initially oxidatively to a reactive intermediate stage, also called quinoneimine or quinonediimine, which then reacts in an oxidative coupling reaction with the couplers to form the particular dye.

Cosmetic agents (M2) therefore contain in addition one or more oxidizing agent (M2-2). Persulfates, peroxodisulfates, chlorites, hypochlorites, and particularly hydrogen peroxide and/or one of its solid adducts to organic or inorganic compounds may be suitable as oxidizing agents.

Methods preferred according to the invention are therefore characterized in that cosmetic agent (M2) includes at least one oxidizing agent (M2-2) from the group comprising persulfates, peroxodisulfates, chlorites, hypochlorites, hydrogen peroxide and its solid adducts to urea, melamine, polyvinylpyrrolidone, and sodium borate, preferably hydrogen peroxide, in a total amount of 0.5 to 10% by weight, preferably of 1 to 10% by weight, in particular of 2 to 10% by weight, based on the total weight of cosmetic agent (M2). If hydrogen peroxide and its solid adducts are used as oxidizing agents, the aforementioned total amount is calculated based on 100% $H_2O_2$.

In a further preferred embodiment, cosmetic agent (M2) is an agent for coloring and optionally simultaneous lightening of keratinic fibers, which includes hydrogen peroxide in a total amount of 0.5 to 15% by weight, primarily 1 to 12.5% by weight, preferably 1.5 to 10% by weight, and in particular 1.5 to 6.5% by weight, based on the total weight of cosmetic agent (M2). The aforementioned total amount of hydrogen peroxide is based in this case on 100% $H_2O_2$.

To achieve an intensified lightening and bleaching effect, cosmetic agent (M2) can contain furthermore at least one peroxo salt. Suitable peroxo salts are inorganic peroxo compounds, preferably selected from the group comprising ammonium peroxodisulfate, alkali metal peroxodisulfates, ammonium peroxomonosulfate, alkali metal peroxomonosulfates, alkali metal peroxodiphosphates, and alkaline earth metal peroxides, and mixtures thereof. Peroxodisulfates, in particular ammonium peroxodisulfate, potassium peroxodisulfate, and sodium peroxodisulfate are particularly preferred.

The aforementioned peroxo salts are contained in a total amount of 0.5 to 20% by weight, primarily 1 to 12.5% by weight, preferably 2.5 to 10% by weight, in particular 3 to 6% by weight, based on the total weight of cosmetic agent (M2).

To prevent a premature, undesirable reaction of the oxidation dye precursors due to the oxidizing agent, oxidation dye precursors and oxidizing agents are expediently produced separately from one another and brought into contact only immediately before use. Oxidative coloring agents are therefore usually offered in the form of a kit consisting of two components (multicomponent packaging unit), wherein the first component includes the oxidation dye precursors and optionally direct dyes, as well as an alkalinizing agent (for example, ammonia), and the second component includes the oxidizing agent.

In a further embodiment of the present invention, therefore, cosmetic agents (M2) are preferred that are characterized in that they are prepared immediately before use by mixing at least two preparations, wherein the at least two preparations are provided in at least two separately produced containers and wherein one container includes a coloring agent (M2a), which includes in a cosmetic carrier at least one oxidation dye precursor, and a further container includes an oxidizing agent preparation (M2b), containing at least one oxidizing agent.

Coloring agent (M2a) in this case preferably includes the oxidation dye precursors, previously given in regard to cosmetic agent (M2), of the developer type and/or coupler type, optionally at least one direct dye, and optionally at least one active substance, auxiliary substance, or additive previously given in regard to cosmetic agent (M2). Oxidizing agent preparation (M2b) preferably includes an oxidizing agent in the form of hydrogen peroxide and/or one of its solid adducts to organic or inorganic compounds, such as urea, melamine, and sodium borate.

Such oxidizing agent preparations (M2b) are preferably aqueous, flowable oxidizing agent preparations. In this case, preferred preparations (M2b) are characterized in that the flowable oxidizing agent preparation (M2b) includes 40 to 90% by weight, primarily 50 to 90% by weight, preferably 55 to 89% by weight, more preferably 60 to 87% by weight, in particular 65 to 85% by weight of water, based on the total weight of oxidizing agent preparation (M2b).

Preferably, the total amount of oxidizing agents, in particular hydrogen peroxide, in oxidizing agent preparation (M2b) is 0.5 to 12% by weight, primarily 1.0 to 10% by weight, in particular 1.5 to 6.0% by weight, based on the total weight of oxidizing agent preparation (M2b). If hydrogen peroxide and its solid adducts are used as oxidizing agents, the aforementioned total amount is calculated based on 100% $H_2O_2$.

According to the invention, oxidizing agent preparation (M2b) can also be applied to the hair together with a catalyst, which activates the oxidation of the dye precursors. Such catalysts are, e.g., certain enzymes, iodides, quinones, or metal ions.

It has proven advantageous, if oxidizing agent preparations (M2b) contain in addition at least one stabilizer or complexing agent for stabilizing the oxidizing agent, in particular hydrogen peroxide. Particularly preferred stabilizers are particularly EDTA and EDDS, and phosphonates, particularly 1-hydroxyethane-1,1-diphosphonate (HEDP), and/or ethylenediamine tetramethylene phosphonate (EDTMP), and/or diethylenetriamine pentamethylene phosphonate (DTPMP), or sodium salts thereof.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for the oxidative dyeing of keratinic fibers, wherein the method comprises the following steps in the indicated sequence:
   a) applying a cosmetic agent (M1) to the keratinic fibers,
   b) allowing agent (M1) to act on the keratinic fibers for a time period of 30 seconds to 40 minutes at a temperature of at least 25° C.,
   c) applying a cosmetic agent (M2) to the keratinic fibers treated with cosmetic agent (M1),
   d) allowing cosmetic agents (M1) and (M2) to act on the keratinic fibers for a time period of 1 to 70 minutes, and
   e) rinsing out of cosmetic agents (M1) and (M2),
   wherein
   cosmetic agent (M1) includes
     at least one oxidation dye precursor of the developer type (M1-1),
     at least one oxidation dye precursor of the coupler type (M1-2),
     at least one direct dye (M1-3), and
     at least one surfactant (M1-4), and cosmetic agent (M2) includes
  at least one oxidation dye precursor (M2-1) and
  at least one oxidizing agent (M2-2).

2. The method according to claim 1, wherein cosmetic agent (M1) in process step b) is allowed to act on the keratinic fibers at a temperature of 25° C. to 120° C. for a time period of 30 seconds to 35 minutes.

3. The method according to claim 1, wherein cosmetic agent (M1) is applied only to individual streaks in process step a).

4. The method according to claim 1, wherein in process step d) cosmetic agents (M1) and (M2) are allowed to act for a time period of 1 to 60 minutes.

5. The method according to claim 1, wherein cosmetic agent (M1) includes the at least one oxidation dye precursor of the developer type (M1-1) in a total amount of 0.0025 to 10.0% by weight based on the total weight of cosmetic agent (M1).

6. The method according to claim 1, wherein cosmetic agent (M1) includes the at least one oxidation dye precursor of the coupler type (M1-2) in a total amount of 0.001 to 6.0% by weight based on the total weight of cosmetic agent (M1).

7. The method according to claim 1, wherein cosmetic agent (M1) includes the at least one direct dye (M1-3) in a total amount of 0.0001 to 6.0% by weight based on the total weight of cosmetic agent (M1).

8. The method according to claim 1, wherein cosmetic agent (M1) includes the at least one surfactant (M1-4) in a total amount of 0.1 to 30% by weight based on the total weight of cosmetic agent (M1).

9. The method according to claim 1, wherein cosmetic agent (M1) has a dynamic viscosity of 10 to 300 mPa*s measured using a Brookfield RDV II+, spindle No. 1, 100 rpm, 20° C.

10. The method according to claim 1, wherein cosmetic agent (M1) is present as a foam and has a liquid separation after 10 minutes of 0.0 to 60.

11. The method according to claim 1, wherein cosmetic agent (M1) has a pH value of 7.0 to 14.0.

12. The method according to claim 1, wherein cosmetic agent (M2) includes as oxidation dye precursor (M2-1) at least one oxidation dye precursor of the developer and/or coupler type.

13. The method according to claim 1, wherein a molar ratio of the quantity of all oxidation dye precursors of the developer type (M1-1) in cosmetic agent (M1) to the total amount of all oxidation dye precursors (M2-1) in cosmetic agent (M2) has a value (M1-1):(M2-1) of 1:5 to 1:2.

14. The method according to claim 13, wherein the molar ratio of the quantity of all oxidation dye precursors of the developer type (M1-1) in cosmetic agent (M1) to the total amount of all oxidation dye precursors (M2-1) in cosmetic agent (M2) has a value (M1-1):(M2-1) of 400:1 to 600:1.

15. The method according to claim 1, wherein cosmetic agent (M1) and cosmetic agent (M2) have identical pH values.

16. The method according to claim 1, wherein cosmetic agent (M2) includes at least one oxidizing agent (M2-2) selected from the group consisting of persulfates, peroxodisulfates, chlorites, hypochlorites, hydrogen peroxide and its solid adducts, urea, melamine, polyvinylpyrrolidone, and sodium borate, in a total amount of 0.5 to 10% by weight.

* * * * *